United States Patent [19]

Kitamura et al.

[11] 4,336,196

[45] Jun. 22, 1982

[54] PROCESS FOR THE PRODUCTION OF PHENYLMALONIC ACID MONO-ESTERS

[75] Inventors: Shigeo Kitamura, Oyabe; Kazuo Yoshioka; Yoshiharu Seriyama, both of Takaoka; Hiroshi Misuta, Toyama, all of Japan

[73] Assignees: Nippon Soda Company Limited, Tokyo; Shionogi Company Limited, Osaka, both of Japan

[21] Appl. No.: 170,910

[22] Filed: Jul. 21, 1980

[30] Foreign Application Priority Data

Jul. 27, 1979 [JP] Japan .................................. 54-95060
Jun. 25, 1980 [JP] Japan .................................. 55-85149

[51] Int. Cl.³ .................. C07D 309/06; C07C 69/773
[52] U.S. Cl. ..................................... 549/416; 560/82; 560/97
[58] Field of Search .................. 260/345.8 R; 560/97, 560/81, 82; 562/423

[56] References Cited

U.S. PATENT DOCUMENTS 2,171,871  9/1939  Walker ................................. 562/423
3,560,531  2/1971  Normant ............................. 562/423
3,976,677  8/1976  Bottaccio et al. ................... 562/423

OTHER PUBLICATIONS

Benkeser et al., Chem. Rev., 57, 867 (1957).
Morrison et al., "Organic Chemistry", publishers, Allan & Bacon, Boston, 3rd. Ed., 1975, pp. 846-853.

Primary Examiner—Nicky Chan
Attorney, Agent, or Firm—George B. Oujevolk

[57] ABSTRACT

Sodium salts of phenylmalonic acid mono-esters are produced by reacting a phenylacetic acid ester with carbon dioxide in the presence of a sodium substituted compound, which is prepared by substituting a sodium atom for a hydrogen atom of an organic compound selected from a group consisting of acetylene, cumene, triphenylmethane, methyl-methylthiomethyl-sulfoxide and dimethyl-sulfoxide, at a temperature in a range of $-20°$ C. to $-40°$ C.

2 Claims, No Drawings

PROCESS FOR THE PRODUCTION OF PHENYLMALONIC ACID MONO-ESTERS

DETAILED DESCRIPTION OF THE INVENTION

BACKGROUND OF THE INVENTION

The present invention relates to a process for the production of phenylmalonic acid mono-esters through carboxylation of phenylacetic acid esters with carbon dioxide.

BRIEF DESCRIPTION OF THE PRIOR ART

Phenylmalonic acid mono-esters are usefull as raw materials for the preparation medicinal preparations such as synthetic penicillin and cephalosporin. In these preparations, phenyl malonic acid mono-esters, 2-[4-(2-tetrahydropyranyloxy)phenyl] malonic acid 4'-methoxybenzyl mono-ester is an important raw material for penicillin and cephalosporin which have a 4-hydroxyphenyl malonic mono-amido radical at 3-position of the β-lactam ring.

The process for the production of phenylmalonic acid mono-esters has been described in Tokkaisho 54-106447 (Number of Japanese patent specification laid open before examination).

In this known process, one hydrogen atom on the α-position of a phenylacetic acid ester is substituted by an alkali metal through the reaction of the ester with an alkali metal salt of hexaalkyl-disilazane, then the alkali metal substituted phenyl acetic acid esters are reacted with carbon dioxide in an inert solvent without moisture at a low temperature to produce alkali metal salts of phenylmalonic acid mono-esters.

In this process, a very expensive material, namely, hexaalkyl-disilazane must be used, and the reaction temperature must be kept at −60° C. or lower in case of preparation of 2-[4-(2-tetrahydropyranyloxy)phenyl] malonic acid 4'-methoxybenzyl mono-ester.

OBJECTS OF THE INVENTION

Accordingly, it is an object of the present invention to provide an economical process for the production of phenylmalonic acid mono-esters by using an activator, which is a sodium substituted compound of acetylene, cumene, triphenylmethane, dimethyl-sulfoxide or methyl-methylthiomethyl-sulfoxide, commercially obtainable in the market at a low price.

It is another object of the present invention to provide an economical process for the production of 2-[4-(2-tetrahydropyranyloxy)phenyl] malonic acid -4'-methoxybenzyl mono-ester by using a more economical reaction temperature, that is −20° C. to −40° C., in comparison with the temperature of −60° C. or lower, of the prior art.

SUMMARY OF THE INVENTION

Briefly stated, the present invention contemplates a process for the production of phenylmalonic acid mono-esters having the following general formula

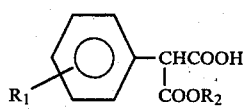

(wherein, $R_1$ is a hydrogen atom, a hydroxy radical, an alkoxy group having 1 to 3 carbon atoms, an acyloxy group having 2 to 4 carbon atoms, an aralkoxy group having a phenyl group, a diphenylmethoxycarbonylmethoxy group, a benzyloxy group substituted by a nitro radical or an alkoxy group having 1 to 3 carbon atoms, or a saturated heterocyclicoxy group, i.e., having oxygen as a hetero-atom in the ring, and $R_2$ is an alkyl group having 1 to 4 carbon atoms, an aralkyl group having a phenyl as the aryl component, diphenylmethyl group, a benzyl group substituted by a nitro radical or an alkoxy group having 1 to 3 carbon atoms, or an indanyl group. Generally speaking, the process comprises reacting a phenylacetic acid esters having the following general formula

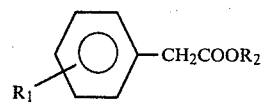

(wherein, $R_1$ and $R_2$ are as stated in the foregoing definitions) with carbon dioxide in the presence of a sodium-substituted compound of an organic compound selected from a group consisting of acetylene, cumene, triphenylmethane, methyl-methyl-thiomethyl-sulfoxide and dimethyl-sulfoxide, at a temperature in a range of −20° C. to −40° C., and neutralizing or weakly acidifying the reaction mixture with acid.

In the present invention, the sodium-substituted compounds are used as the activator of the carboxylation reaction. Sodium-acetylene is easily produced by introducing acetylene gas into dispersed metal sodium in an inert organic solvent such as kerosene, toluene and xylene at a room temperature, and all of the other activators are prepared by dropping a mixture of monochlorobenzene and any one of said compounds except acetylene, in about equal mole ratio, into sodium dispersion containing 2 to 3, more preferably, 2.3 to 2.7 mole equivalent of sodium with respect to the mono-chlorobenzene in an inert solvent at a room temperature and then heating the components. Sodium-sulfoxides are also easily produced by reacting the sulfoxides with a sodium amide or a sodium hydride at 50° C.-70° C.

In the present invention, the phenylacetic acid esters are mixed with a dispersion or suspension of the activator in an inert organic solvent such as kerosene, toluene and xylene, and then the mixture in cooled to a temperature of −20° C. to −40° C., more preferably about −30° C. Sodium salts of phenylmalonic acid monoesters are formed by introducing carbon dioxide, as carbon dioxide gas or dry ice, into the mixture at the foregoing temperature. All of these operations must be conducted under moisture-proof conditions.

Into the reaction mixture thus obtained, an appropriate quantity of a saturated sodium chloride aqueous solution and an organic solvent such as toluene, n-hexane and a mixed solvent thereof are added at a temperature of −10° C. to +10° C. or so, then sodium salts of phenylmalonic acid mono-esters are precipitated from the mixture as crystals. Those crystals are separated by filteration, and then added to a mixture of water and organic solvent such as alkyl acetate to be nutralized or weakly acidified by an inorganic acid. After neutralization, the organic layer is separated from the mixture and washed by water. The desired compounds of phenylmalonic acid mono-esters are obtained by removing the solvent, by evaporation, from the separated organic layer.

The present invention provides an industrially preferable and economical process for the production of phenylmalonic acid mono-esters because the yields of the objective products are good and the prices of the raw materials for the activator are reasonably low and easily obtainable in the market and the reaction temperature is not exceedingly low which contributes to saving energy.

The present invention will be more clearly understood by refering to the following examples, however, these examples are intended to illustrate the invention and are not to be construed to limit the scope of the invention.

EXAMPLE 1

26 gr (216 m mol) of cumene was added into 40% sodium dispersion in kerosene containing 4.7 gr (205 m mol) of metal sodium, and the mixture was stirred uniformly. 9 gr (80 m mol) of mono-chlorobenzene was dropped into the above mixture and kept at a temperature of 10° C. to 20° C., and then the mixture was heated to 110° C. and kept at said temperature for about 2 hours.

Into the mixture, 30 ml of toluene solution containing 7.12 gr (20 m mol) of 4-(2-tetrahydropyranyloxy)phenyl acetic acid 4'-methoxybenzyl ester was added at room temperature, and the mixture was stirred for 30 minutes, and then 30 ml of toluene was added thereinto, and cooled to −30° C. 20 gr of dry ice was slowly added into the cooled mixture maintained at the same temperature. After completion of the reaction, the mixture was heated to 0° C., and then 100 ml of saturated sodium chloride aqueous solution and 90 ml of n-hexane were added thereinto. Sodium salt of 2-[4-(2-tetrahydropyranyloxy)phenyl]malonic acid 4'-methoxybenzyl mono-ester was precipitated, as crystals, in the water layer. The crystals were separated by filtration, and then washed by a mixed solvent of toluene and n-hexane (toluene:n-hexane=1:1 by volume).

The crystals were dispersed into 200 ml of water, and 150 ml of ethyl acetate was added into the dispersing mixture, and then the mixture was adjusted to an acidity of PH 3 to 4 adding a 10% phosphoric acid aqueous solution.

The organic solvent layer was separated from the water layer and the organic layer was washed by water, and dried by adding sodium sulfate anhydride.

6.7 gr of 2-[4-(2-tetrahydropyranyloxy)phenyl]malonic acid 4'-methoxybenzyl mono-ester was obtained from the organic layer by evaporation. The melting point was 115° C.–117° C., and the yield was 83%.

EXAMPLE 2

Acetylene gas was slowly introduced into a 30% sodium-kerosene dispersion containing 4.7 gr (205 m mol) of metal sodium at a room temperature. 60 ml of toluene solution containing 14.24 gr (40 m mol) of 4-(2-tetrahydropyranyloxy) phenylacetic acid 4'-methoxybenzyl ester was added into the above mixture. Thereafter, the mixture was treated according to the same procedure as shown in Example 1, except for using double quantities of those shown in said example such as dry ice, saturated sodium chloride aqueous solution, n-hexane, water, ethyl acetate, solvents, and so on.

13.5 gr of 2-[4-(2-tetrahydropyranyloxy)phenyl]malonic acid 4'-methoxybenzyl mono-ester was obtained. The melting point was 114° C.–117° C., the yield was 84%.

EXAMPLE 3

30 ml of toluene solution containing 9 gr (80 m mol) of mono-chlorobenzene was added into 40% sodium-kerosene dispersion containing 4.7 gr (205 m mol) of metal sodium, and 30 ml toluene solution containing 19.5 gr (80 m mol) of triphenylmethane were added into the above dispersing mixture.

30 ml of toluene solution containing 7.12 gr (20 m mol) of 4-(2-tetrahydropyranyloxy)phenyl acetic acid 4'-methoxybenzyl ester was added into the above mixture, and thereafter, the mixture was treated according to the same procedure shown in Example 1.

6.5 gr of the desired material was obtained.
m.p.; 115° C.–117° C., yield; 81%.

EXAMPLE 4

Methyl methylthiomethyl-sulfoxide was used instead of triphenylmethane in Example 3.

The desired compound was obtained by following the same procedure as shown in Example 3, except for the changes described.
m.p.; 115° C.–117° C., yield; 82%.

EXAMPLE 5

Dimethyl-sulfoxide was used instead of triphenylmethane in Example 3.

The desired material was obtained by following the same procedure described in Example 3, except for the changes described.
m.p.; 115° C.–117° C., yield; 81.5%.

EXAMPLE 6

A dispersion of 7.2 gr (65 m mol) of dimethyl-sulfoxide sodium-substituted compound was prepared by reaction of 3.1 gr (80 m mol) of sodium amide with 9 gr (115 m mol) of dimethyl sulfoxide in toluene at 70° C. under argon atmosphere. 7.12 gr (20 m mol) of 4-(2-tetrahydropyranyloxy)phenyl acetic acid 4'-methoxybenzyl ester was added into 30 ml of the dispersion of sodium-dimethyl sulfoxide and then 30 ml of toluene was added into the mixture. Thereafter, the mixture was treated by following the same procedure described in Example 1.

6.5 gr of 2-[4-(2-tetrahydropyranyloxy)phenyl] malonic acid 4'-methoxy benzyl mono-ester was obtained.
m.p.; 115° C.–117° C., yield; 81%.

EXAMPLE 7

According to the following reaction equation

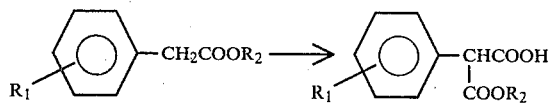

various products were obtained by reaction of phenyl acetic acid esters having $R_1$ and $R_2$ which are defined herein, the process steps of the reactions and other details are as described in Example 6. The results are shown on the following table:

| Example No. | R₁ (phenyl group) | R₂ | melting point (°C.) | IR: $v_{max,cm^{-1}}^{Nujol}$ | NMR: $\sigma_{ppm}^{CDCl_3}$ | elemental analysis | yield (%) |
|---|---|---|---|---|---|---|---|
| 7-1 | phenyl | —CHPh₂ | 120 ~ 120.5 | | 4.77(S,1H),6.93(S,1H), 7.3(15H),10.53(S,1H) | | 80 |
| 7-2 | " | —PNB | 135 ~ 136 | 3000 ~ 3300 br, 1750 1722, 1667 | 4.87(S,1H),5.30(S,2H), 7.38(brs,5H),7.50, 8.16A₂B₂(9Hz)4H(CD₃CD) | | 80 |
| 7-3 | " | indanyl | 82 ~ 83 | 1760, 1725 | 2.13q(8Hz)2H, 2.90t(8Hz)4H,4.93S1H, 6.77~7.70m8H, 9.87s1H | (as C₁₈H₁₆O₄) Calculated(%): C,72.96;H,5.44 Analysed(%): C,73.00;H,5.61 | 82 |
| 7-4 | HO—phenyl— | —CHPh₂ | 153 ~ 154 | | 4.83(S,1H),6.82t 7.32ABq(8Hz)4H, 6.88(S,1H);7.32(10H), 9.42(brs,1H) (d₆-acetone) | | 78 |
| 7-5 | " | -t-Bu | 109 ~ 110 | 3570, 3500 ~ 3000br, 1728 (CHCl₃) | 1.43(S,9H),4.47(S,1H), 6.77~7.37m6H | | 76 |
| 7-6 | " | indanyl | 110 ~ 115 | 3425, 1750, 1700(KBr) | 2.00(m,2H),2.80t, (6Hz)4H,4.82(S,1H), 6.63~7.43(m,7H) (CD₃OD) | | 75 |
| 7-7 | MeO—phenyl— | —CHPh₂ | | | 3.78(S,3H),4.75(S,1H), 6.82~7.42(m,15H),8.23 (S,1H) | | 81 |
| 7-8 | AcO—phenyl— | " | | | 2.25(S,3H),4.78(S,1H), 6.95 7.6(15H), (S,1H) | | |
| 7-9 | PhCH₂O—phenyl— | " | 106 107 | 3000(br), 1735, 1690 | 4.50(S,1H),4.92(S,2H), 5.06(S,2H),6.84, 7.27A₂B₂(9Hz)4H, 7.80(brs,1H) | | 80 |
| 7-10 | " | -t-Bu | | 3500 3000 br, 1728br, (CHCl₃) | 1.42(S,9H),4.53(S,1H), 5.10(S,2H),6.90~7.37(m, 4H),7.43(S,5H),10.22 (brs,1H) | | 81 |
| 7-11 | Ph₂CHO— COCH₂O—phenyl— | —CHPh₂ | | 1760, 1735, 1720(CHCl₃) | 4.70(brs,3H) | | |
| 7-12 | PMBO—phenyl— | —CHPh₂ | 99 ~ 106 | | 3.80(S,3H),4.72(S,1H), 4.98(S,2H),6.83~7.43(m, 19H),8.90(S,1H) | | 85 |
| 7-13 | " | —PMB | 128 ~ 130 | 3260, 1740, 1612, 1585, 1511, 1250, 1168(KBr) | 3.78(S,6H),4.75(S,1H), 5.05(S,2H),5.15(S,2H) (d₆-acetone) | | 90 |
| 7-14 | OPMB phenyl | " | 102 ~ 104 | 1742br | 3.75(S,6H),4.92(S,2H) 5.07(S,3H),6.70~7.47(m, 12H),10.03(brs,1H) | | 75 |
| 7-15 | OPMB phenyl | " | 96 ~ 98 | 1734br | 3.78(S,3H),3.82(S,3H), 4.67(S,1H),4.93(S,2H), 5.15(S,2H),6.70~7.50 (m,12H),9.35(brs,1H) | | 84 |
| 7-16 | OPMB, PMBO—phenyl— | " | 122 ~ 123 | | 3.75(S,9H),3.80(S,9H), 4.60(S,1H),4.90(S,2H), 5.13(S,4H),6.83~7.50(m, 15H) | (as C₃₃H₃₂O₉) Calculated(%): C,69.22;H,5.63 Analysed(%): C,69.20;H,5.68 | 83 |
| 7-17 | OPMB, OPMB phenyl | —CHPh₂ | | 1740 (CHCl₃) | 3.72(S,6H),3.73(S,6H), 6.77(S,4H),4.83(S,4H), 5.20(S,1H),6.7~7.4(m, 12H),9.5(br,1H) | | 75 |

| Example No. | $R_1$ | $R_2$ | melting point (°C.) | IR: $v^{Nujol}_{max,cm^{-1}}$ | NMR: $\sigma^{CDCl_3}_{ppm}$ | elemental analysis | yield (%) |
|---|---|---|---|---|---|---|---|
| 7-18 | CH₃O PMBO—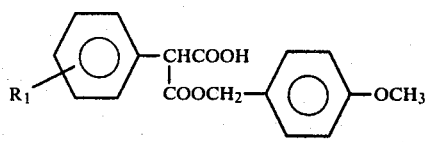 | —PMB | 126 ~ 127.5 | | 3.78(S,9H),3.82(S,9H), 4.77(S,1H),5.05(S,2H), 5.17(S,2H),6.83~7.60(m, 11H) (d₆-acetone) | (as C₂₆H₂₆C₈) Calculated(%): C,66.94;H,5.62 Analysed(%): C,66.85;H,5.68 | 85 |

NOTE:
Ph = phenyl
PNB = P-nitro benzyl
PMB = P-methoxy benzyl

What is claimed is:

1. A process for the production of phenylmalonic acid mono-esters having the following general formula:

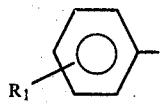

wherein

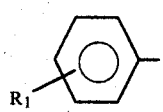

is phenyl mono-substituted by 2-tetrahydropyranyloxy or p-methoxybenzyloxy or is disubstituted by p-methoxybenzyloxy or p-methoxybenzyloxy and methoxy, which process consits of reacting phenylacetic acid esters having the following formula:

wherein has the foregoing definition, with carbon dioxide in the presence of a sodium-substituted compound of an organic compound selected from the group consisting of acetylene, cumene, methyl-methyl-thiomethyl-sulfoxide and dimethyl-sulfoxide at a temperature of from about −20° C. to about −40° C., and neutralizing or weakly acidifying the reaction mixture with acid.

2. A process according to claim 1 wherein the sodium-substituted compound of an organic compound is cumene or dimethyl-sulfoxide.

UNITED STATES PATENT AND TRADEMARK OFFICE
CERTIFICATE OF CORRECTION

PATENT NO. : 4,336,196
DATED : June 22, 1982
INVENTOR(S) : Shigeo Kitamura, et al It is certified that error appears in the above-identified patent and that said Letters Patent is hereby corrected as shown below:

Column 7, line 38, claim 1, "consits" should read --consists--.

Signed and Sealed this

Twenty-second Day of March 1983

[SEAL]

Attest:

GERALD J. MOSSINGHOFF

Attesting Officer

Commissioner of Patents and Trademarks